United States Patent [19]

Hunter et al.

[11] Patent Number: 5,043,032
[45] Date of Patent: Aug. 27, 1991

[54] METHOD FOR DETECTING PROTECTIVE LAYER ON COMPOSITE MATERIALS

[75] Inventors: Bobby J. Hunter, Forth Worth; Coy P. Rhine, Weatherford, both of Tex.

[73] Assignee: Bell Helicopter Textron Inc., Forth Worth, Tex.

[21] Appl. No.: 455,455

[22] PCT Filed: Feb. 17, 1989

[86] PCT No.: PCT/US89/00587

§ 371 Date: Feb. 17, 1989

§ 102(e) Date: Feb. 17, 1989

[87] PCT Pub. No.: WO90/09584

PCT Pub. Date: Aug. 23, 1990

[51] Int. Cl.$^5$ .............................................. G01D 21/00
[52] U.S. Cl. ...................... 156/64; 156/378; 324/231
[58] Field of Search ............... 73/159, 160; 156/64, 156/378; 324/222, 230, 231

[56] References Cited

U.S. PATENT DOCUMENTS 1,697,142 11/1929 Roller .
1,777,309 10/1930 Hopkinson .
2,601,336 6/1952 Smith-Johannsen .
3,187,071 6/1965 Radziejowski .
3,287,197 11/1966 Errede .
3,481,812 12/1969 Holub et al. .
3,755,730 8/1973 Vogelgesang .
3,893,022 2/1975 Kulik et al. .
4,134,538 1/1979 Lagarde et al. .
4,297,159 10/1981 Dobias et al. .
4,349,402 9/1982 Parker .
4,428,523 1/1984 Snitzer et al. .
4,543,295 9/1985 St. Clair et al. .
4,582,556 4/1986 Butt et al. .
4,642,161 2/1987 Akahoshi et al. .
4,670,080 6/1987 Schwarz et al. .
4,702,785 10/1987 Burger .
4,763,071 8/1988 McGee et al. .
4,801,496 1/1989 Buchacher .
4,803,022 2/1989 Barrell et al. .
4,814,703 3/1989 Carr et al. .
4,876,153 10/1989 Thorfinnson ............... 156/289 X

OTHER PUBLICATIONS

International Search Report, PCT/6589/00587

Primary Examiner—David A. Simmons
Assistant Examiner—James J. Engel, Jr.
Attorney, Agent, or Firm—Richards, Medlock & Andrews

[57] ABSTRACT

A protective backing for composite sheets and a method of detecting the presence of protective backing within a stack of composite sheets. The protection of the surfaces of uncured composite sheets is provided by applying a protecting backing having a metal component to the composite sheet, which is removed prior to layup and curing of a composite laminate. Presence of the protective backing in a layup of composite sheets or a laminate made from the layup composite sheets may be detected by passing them through a sensing presence of an eddy current.

7 Claims, 1 Drawing Sheet

METHOD FOR DETECTING PROTECTIVE LAYER ON COMPOSITE MATERIALS

TECHNICAL FIELD

This invention relates to the detection of surface protective backings which may be present in the lamination of composite materials, and to provide a method to apply protective backings to composite materials which can be detected automatically.

BACKGROUND OF THE INVENTION

The use of composite materials has increased in recent years. Composites are very attractive because they offer unique properties and the structure of the composites as well as laminates of the composites can be tailored to meet specific performance requirements. Composites are based on the controlled distribution of reinforcement, which may consist of one or more materials, in a continuous phase of a matrix material. Orientation of the reinforcement affects the strength of composite and can produce high unidirectional strength. To acquire optimum overall strength, layers of composite materials are often laminated such that the orientation of the reinforcement elements of the several layers run in different directions to provide optimum strength in more than one direction.

An initial preparation of a laminate is to prepare a composite sheet. The composite sheet is formed by arranging the reinforcement material in the desired manner and cover the reinforcement with the matrix system. This is then typically rolled or otherwise handled to spread the reinforcement evenly and to produce a uniform thickness for the sheet. This creates an impregnated system which is then partially cured to fix the geometry while allowing enough shape relaxation (drape) and adherence (tack) to permit complex shapes to be built up from the composite sheets thus formed. These composite sheets are commonly called "prepreg" in the industry. A prepreg can also be formed from a woven cloth of the reinforcing material which is then impregnated with resin. When these prepreg sheets are not used immediately to make a desired structure, the surfaces of the sheet are covered with a protective backing to protect the part ally cured sheet.

In the typical fabrication of complex parts, multiple sheets of prepreg are overlayed in the desired orientation. This process is called layup. After layup, the structure formed is cured, thereby bonding the sheets of composite in a laminate. In order to achieve proper bonding of the prepreg composite sheets together to form the laminate, it is important that the surfaces of the prepreg be free from contamination which would interfere with the curing of the laminated structure. Because the prepregs are usually made in a different processing step, the partially cured prepreg material is generally covered with a protective sheet of material to prevent contamination and damage to the prepreg. These coatings are referred to as protective backings. Typical backings used with prepregs have been plastic films such as polyethylene, mylar, and tedlar. These protective backings are later removed prior to the layup procedure. After a part is laid up in the desired shape, the laminate of prepreg material is then subject to final cure which bonds all the prepreg sheets into the single laminated part. In the event that backing material is inadvertently left on a prepreg sheet during layup, the layers of prepreg adjacent to that backing will not properly cure and thus not bond completely resulting in a weakened area of the laminated part. Thus, it is important to assure that all backing material is removed and that the layup does not contain any backing. The backings currently used can only be reliably detected by visual inspection of the laid up structure which is costly and subject to error, especially when a portion of backing material is located in the layup where it can not be visually observed. Thus, there has been a continuing need for an automated system to detect backing materials inadvertently left in layups prior to curing.

The present invention has the technical advantages of providing a backing which can be detected by automated means, thereby greatly improving reliability and speed of inspection. Further, the present invention provides a quality control measure which can be used both prior to and after cure.

SUMMARY OF THE INVENTION

In one aspect the present invention relates to rendering the protective backing on prepreg sheets of composite material detectible by automated systems. Backings are rendered detectible by utilizing a backing with sufficient metallic content to be detectible by an induced eddy current field. An eddy current field is produced by generating a magnetic field over the metal which creates an eddy current within the metal which induces an eddy current field which can be detected. Backings may be rendered detectible by forming the backing from one or more films of a polymeric material laminated to a metallic film, or a polymeric film which has a metallic film deposited thereon by vacuum deposition, spray deposition or other methods. Also, the backing sheet of the polymeric film already applied to a composite sheet may be rendered detectible by adhering to the sheet a strip of foil which will interrupt a magnetic field.

In another aspect, the present invention relates to a method for detecting the presence of a backing film which may be present on one or more sheets of composite material in a stack of a multiplicity of composite sheets to be laminated together. The process involves passing an uncured stack of a predetermined number or less composite sheets to be laminated through a magnetic field and sensing the presence, if any, of induced eddy current fields to determine the presence of backing material within the stack of composite material. The process can also include the step of calibrating the detector to detect the presence of a single backing located within a predetermined number of composite sheets which have been stacked one upon another.

In another aspect, the present invention involves a quality control inspection method by passing an uncured or cured composite laminate structure through a magnetic field and sensing the presence or absence of induced eddy current fields to determine the presence of metal within the laminated composite.

DETAILED DESCRIPTION OF A PREFERRED EMBODIMENT

Figure 1:
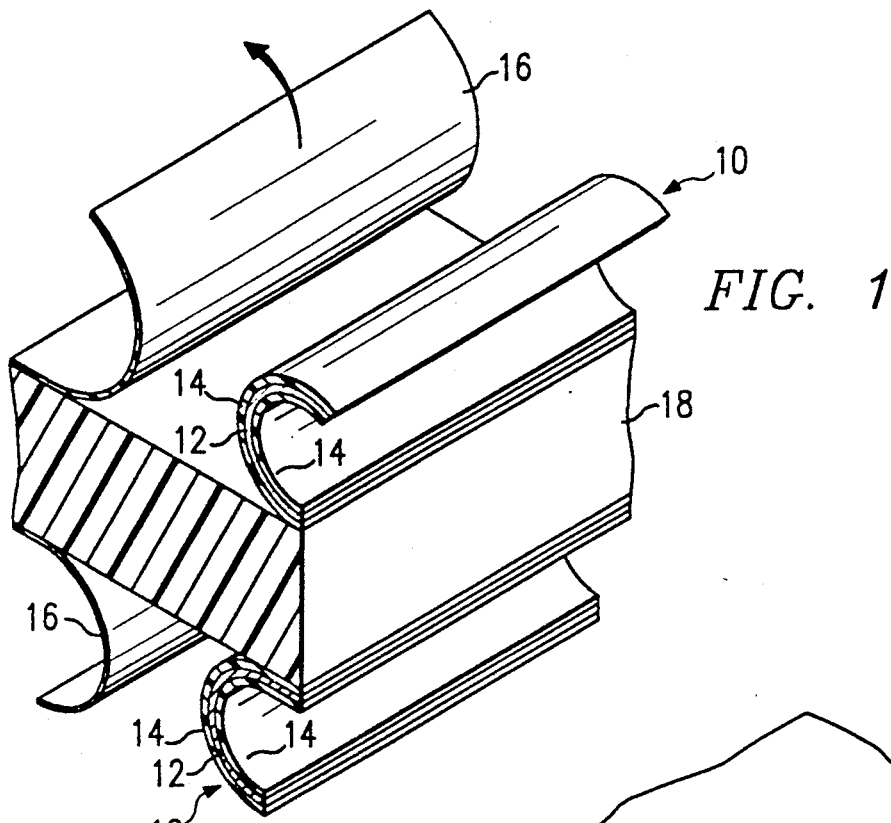
FIG. 1 is a cross sectional view of a composite material covered by the protective backing layer to which a foil strip has been applied.

FIG. 1 illustrates a section of a sheet of prepreg composite material 10 having adhered to each side of the sheet a protective backing 12. Note the drawings are not to scale and the prepreg sheets have a length and width substantially in excess of the thickness of the sheet. Generally sheets of prepreg composite material have a thickness of less than about 0.010 inches. As described above, prepreg composite material contains the reinforcing elements and partially cured matrix. The partially cured matrix is protected prior to fabrication by a protective backing or backings. In the past, these protective backings were generally films of a polymeric material such as polyethylene film, mylar film or polyester film. These films are very thin, generally less than 0.003 inches in thickness. Prior to fabrication of the laminate, the protective films are intended to be removed, thus, exposing the uncured resin of the composite sheet. Failure to remove these prior polymeric protecting backings during layup of the laminate resulted in defects in the final product. In accordance with the present invention, such sheets received from suppliers may be rendered detectible in accordance with the present invention by the application of one or more strips 10 composed of a metal foil 12 laminated to a polymeric layer 14 to the protective backings 16 of prepreg material 18 as it is received from suppliers. The strip may also be a metallic foil laminated between two layers of polymeric material and then adhered to the backing. A sheet, rather than a strip, may be applied. As shown in the preferred embodiment, the metal is covered by a polymeric so that if a composite sheet is laid in contact with the strip it will not contact any metal which may contaminate the prepreg. Preferably, however, detectible protective backings are applied to the prepreg sheet at the time of its manufacture.

Figure 2:
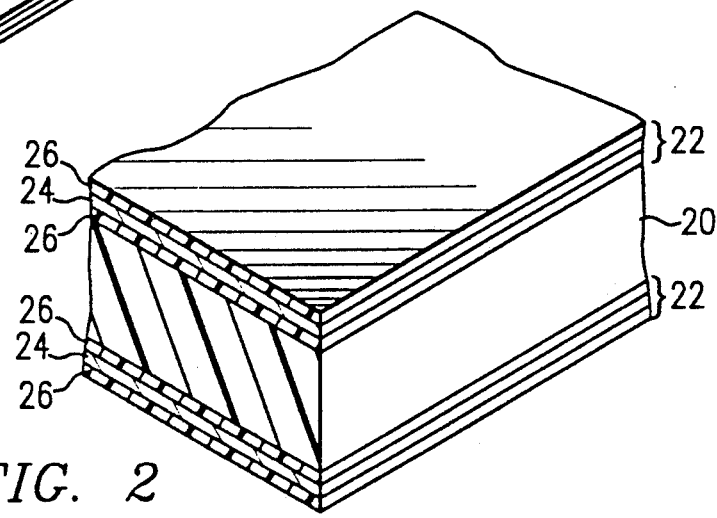
FIG. 2 is a cross sectional isometric view of a composite material covered by protective backing layers containing a metallic component.

FIG. 2 illustrates a prepreg sheet of composite material 20 having protective backings 22 applied to each side of sheet 20. The protective backings 22 illustrated are laminate films made from a film of metal foil 24 laminated between two polymeric films 26 made of a polymeric material, such as polyethylene or polyester. A suitable protective backing film can be formed from a film of aluminum foil approximately 0.00035 inches in thickness laminated between two films of low density polyethylene, each polyethylene film being about 0.00345 inches in thickness. The protective backing can be made of any metallic foil laminate and may be a laminate of a sheet of metallic foil with a polymeric sheet laminated only to one side, however, it is preferred that the metal be covered on both sides by a polymeric layer. The metallic layer needs to be of sufficient thickness that it produces a detectible eddy current field when subjected to a magnetic field. A detectible backing can also be made from a film of polyethylene, polyester or other polymeric material upon which metal has been spray or vacuum deposited with another polymer laminated to it. Any metallic coating which is detectible by an eddy current field such as aluminum or copper can be used. The preferred coating is aluminum for economic reasons. Preferably, the metallic content of the backing whether foil or coating should be of sufficient mass to be detectible through 20 or more layers of composite sheets having a thickness of about 0.007 to 0.10 per sheet. Also, it is preferable that the metallic content be evenly distributed throughout the backing. Thus, if a small portion of backing rips out of the back when it is removed from the composite sheet, it will be detectible. Furthermore, uneven distributions of the metallic content may produce undesired variations in the eddy current field.

Figure 3:
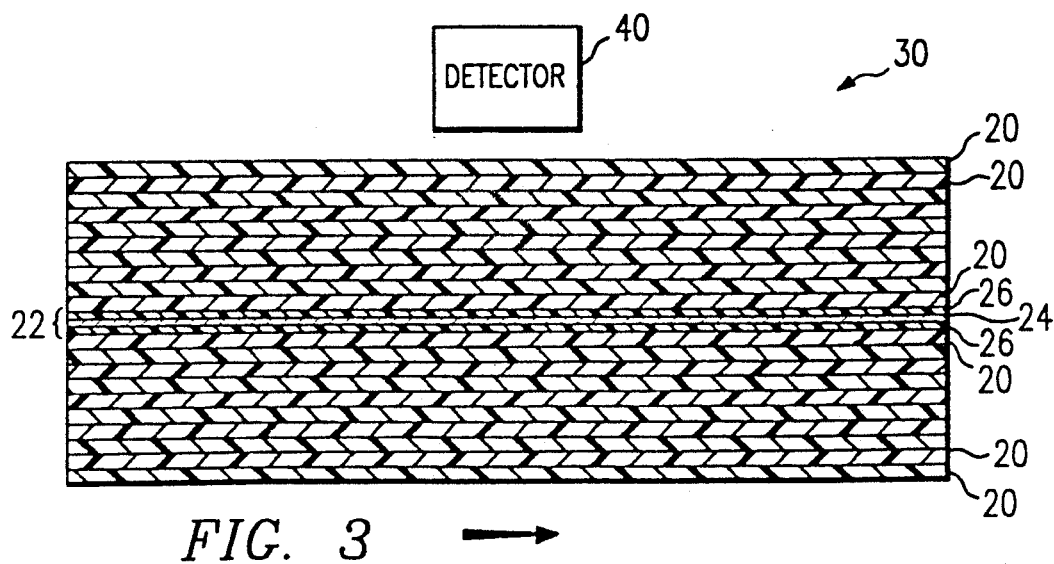
FIG. 3 is a view of a stack of composite material containing a protective backing layer interposed passing through a magnetic field.

FIG. 3 shows a cross sectional view of a layup generally indicated as 30. The layup is comprised of a stack of composite sheets 32 oriented in a predetermined fashion. Interposed in the stack of sheets 32 is a backing sheet 34 which was inadvertently not removed from one side of one of the composite sheets 32. Backing sheet 34 is a laminate of two polymeric layers 36 and a metallic layer 38. The backing has a detectible metal content. The uncured layup structure 30 is passed under a conducting probe 36 positioned above the structure 30. The probe may be positioned above or below the stack. The probe generates a magnetic field which induces a current in the metallic content of backing 34 thereby inducing an eddy current field. The sensing of this eddy current is monitored and triggers an alarm or presents a readout on an oscilloscope indicating the presence of the backing material. In the event backing film is detected the layup structure may then be disassembled and the backing sheet removed, the layup structure can then be reassembled without any backing sheets and passed to the curing step. The layup structure is then cured to bond composite sheets 32 into a final laminated composite product.

The method of the invention can also be utilized after curing to provide another quality control test. The cured laminated structure is passed by a probe which generates a magnetic field, which will induce an eddy current field in the backing material containing metal which can be sensed and determined. If backing is detected in the cured structure, the structure may be discarded or appropriately marked for use in an application, if any, suitable for such a substandard product.

The present invention is useful for testing laminate made of non-metallic composite, such as resin impregnated fiberglass cloth or resins containing graphite or carbon fiber reinforcement. These non-metallic composites are widely used in the aerospace industry and the detection of defects in laminates is very important.

Known eddy current detecting apparatus, such as the Nortec Model 23 Eddyscope sold by Stavley Instruments, Irving, Tex., can be useful in the present invention. Detection can be affected by the thickness of the structure surrounding the metallic content to be detected. Frequently laid up structures are formed from the laminations of over 40 separate sheets of composite material. Thus, a protective backing film inadvertently not removed from a composite sheet may be located in the layup of the lamination which may be covered by a number of composite sheets, such as 20 or more sheets. Detection is also affected by the type of metallic content, whether a foil, deposited film, or strip of metal as well as the type of metal. Thus, the detector is calibrated to have sufficient sensitivity to pick up the metal utilized on a single backing sheet when that backing sheet is included in a stack of a predetermined number of composite sheets. Preferably, this calibration is accomplished utilizing a number of composite sheets equal to or in excess to the number of composite sheets to be laid up. For example, if 40 sheets of composite material are to be laminated one can place a sample of the backing film which is used on a composite sheet which is on top of a stack of 25 other composite sheets and cover the backing film with another 25 sheets of composite material. The backing can also be placed at the bottom of the stack and the probe at the top of the stack. The sample is then put under the probe and the detector adjusted such that the eddy current field caused by the backing film will be sensed and be the signal sufficient to monitor.

EXAMPLE

Composite sheets of 8 ply reinforcing material have a thickness of about 0.56 inches and 6 inches in length by 6 inches in width were utilized for the testing. Also utilized for the testing was a backing film which was a lamination of an aluminum foil between two films of polyethylene. The aluminum foil was approximately 0.00035 inches in thickness and the polyethylene films were approximately 0.00345 inches in thickness thus the backing film had an overall thickness of about 0.0038 inches. The backing film was cut into squares one-half inch wide and one-half inch in length. A layup was then made utilizing 48 plies of composite material sheets with a layer of backing material interspersed at random locations between every eight plies of composite material in the 48 ply laminate while in an uncured condition. The uncured laminate was then passed under the probe of Nortec Model 23 Eddyscope, eddy current detector. The presence of the backing film was detected as the eddy current detector passed over the laminate and could be observed on the oscilloscope of the detector.

The same specimen was then cured and retested with the eddy current detector and all of the backing film implants were again detected. Thus, demonstrating the suitability for the test both as a pre- and post-curing quality control measure.

In another series of tests, backing material sold under the trade name Scotchpack 10, which is a film of polyester approximately 0.003 inches of thickness were utilized. A composite laminate containing implants of this film was also made as before and was passed under the eddy current detector and the backings could not be detected. Thus, if the laminate had been cured the backing materials would have gone undetected and produced a defective final cured structure.

Having described a few embodiments and advantages of the present invention, it will be apparent to those skilled in the art that modifications and adaptions may be made without departing from the scope of the invention.

What is claimed is:

1. A method of detecting backing material in stacks of composite sheets comprising:
    (a) passing a stack of composite sheets to be cured to form a laminate of composite sheets through a magnetic field; and
    (b) sensing for the presence of eddy current fields as the stack is passed through said magnetic field to thereby determine the presence of backing material within said stack.

2. A method of detecting backing material in stacks of composite sheets comprising:
    (a) calibrating an eddy current detector to detect the presence of a single protective backing film having a metallic content within a stack of a predetermined number of composite sheets;
    (b) forming a layup of composite sheets, the number of sheets being equal to or less than said predetermined number of composite sheets;
    (c) passing said layup through a magnetic field; and
    (d) sensing for the presence of eddy current fields to determine the presence of backing film within said layup.

3. The method of claim 2 wherein said metallic content is a non-ferrous metal.

4. The method of claim 3 wherein said non-ferrous metal is aluminum.

5. The method of claim 2 wherein said protective backing film is a laminate of a metal foil with one or more polymeric films.

6. The method of claim 5 wherein said metal foil is about 0.00035 inches thick or greater.

7. The method of claim 2 wherein said protective backing film is a laminate of a film of aluminum foil between sheets of low density polyethylene.

* * * * *

UNITED STATES PATENT AND TRADEMARK OFFICE
CERTIFICATE OF CORRECTION

PATENT NO. : 5,043,032                                    Page 1 of 6

DATED : August 27, 1991

INVENTOR(S) : Hunter, et al.

It is certified that error appears in the above-identified patent and that said Letters Patent is hereby corrected as shown below:

Title page, left column, line [75], delete "Forth" and insert therefore --Fort--.

Title page, left column, line [73], delete "Forth" and insert therefore --Fort--.

Abstract
delete the first word "A" and insert therefore --The present invention is a--.

Abstract
after "through a " insert --magnetic field and--.

Column 1, line 21,
before "composite" insert --the--.

Column 1, line 31,
delete "cover" and insert therefore --covering--.

Column 1, line 45,
and insert therefore --partially--.

Column 2, line 1, after "completely" insert --.--.

UNITED STATES PATENT AND TRADEMARK OFFICE
CERTIFICATE OF CORRECTION

PATENT NO. : 5,043,032
DATED : August 27, 1991
INVENTOR(S) : Hunter, et al

It is certified that error appears in the above-identified patent and that said Letters Patent is hereby corrected as shown below:

Column 2, line 1,
delete "resulting" and insert therefore --This results--.

Column 2, line 26,
after "metal" insert --,--.

Column 2, line 27,
after "metal" insert --.--.

Column 2, line 27,
delete "which" and insert therefore --This--.

Column 2, line 51,
delete "one upon" and insert therefore --upon one--.

Column 3, line 5, after
"having" insert --a protective backing 12--.

Column 3, line 6, after
sheet" delete "a protective backing 12".

Column 3, line 9, after
"Generally" insert --,--.

Column 3, line 20,
after "thus" delete ",".

Column 3, line 22,
delete "resulted" and insert therefore --results--.

UNITED STATES PATENT AND TRADEMARK OFFICE
CERTIFICATE OF CORRECTION

PATENT NO. : 5,043,032
DATED : August 27, 1991
INVENTOR(S) : Hunter, et al

It is certified that error appears in the above-identified patent and that said Letters Patent is hereby corrected as shown below:

Column 3, line 34,
after "polymeric" insert --layer--.

Column 3, line 40, delete " . ".

Column 3, line 52,
after "side" delete ", however" and insert therefore --. However--.

Column 3, line 59,
delete "spray" and insert therefore --sprayed--.

Column 3, line 61,
after "field" insert --,--.

Column 3, line 62,
after "copper" insert --,--.

Column 3, line 64,
after "backing" insert --,--.

Column 3, line 64,
after "coating" insert --,--.

UNITED STATES PATENT AND TRADEMARK OFFICE
CERTIFICATE OF CORRECTION

PATENT NO. : 5,043,032

DATED : August 27, 1991

INVENTOR(S) : Hunter, et al

It is certified that error appears in the above-identified patent and that said Letters Patent is hereby corrected as shown below:

Column 4, line 23,
after "detected" insert --,--.

Column 4, line 24,
delete "removed the" and insert therefore --removed. The--.

Column 4, line 49 (page 11, line 16), after "Frequently" insert --,--.

UNITED STATES PATENT AND TRADEMARK OFFICE
CERTIFICATE OF CORRECTION

PATENT NO. : 5,043,032
DATED : August 27, 1991
INVENTOR(S) : Hunter, et al

It is certified that error appears in the above-identified patent and that said Letters Patent is hereby corrected as shown below:

Column 4, line 56,
after "strip of metal" insert --,--.

Column 4, line 63,
after "excess" delete "to" and insert therefore --of--.

Column 4, line 65,
after "laminated" insert --,--.

Column 5, line 5,
delete "be the" and insert therefore --register a--.

Column 5, line 9, after
"material" delete "have".

Column 5, line 9, after
"material" insert --6 inches in length by 6 inches in width and--.

Column 5, line 10,
delete "and 6 inches in length by".

Column 5, line 11,
delete "6 inches in width".

Column 5, line 17,
after "thickness" delete "thus" and insert therefore --. Thus,--.

Column 5, line 22,
delete "a layer" and insert therefore --layers--.

UNITED STATES PATENT AND TRADEMARK OFFICE
CERTIFICATE OF CORRECTION

PATENT NO. : 5,043,032
DATED : August 27, 1991
INVENTOR(S) : Hunter, et al

It is certified that error appears in the above-identified patent and that said Letters Patent is hereby corrected as shown below:

Column 5, line 27, before "Nortec" insert --a--.

Column 5, line 27, after "Eddyscope" delete ",".

Column 5, line 33, after "detected" delete ". Thus," and insert therefore --, thus--.

Column 5, line 39, after "inches" delete "of thickness were" and insert therefore --thick, was--.

Signed and Sealed this

Twenty-first Day of June, 1994

BRUCE LEHMAN

*Attest:*

*Attesting Officer*          Commissioner of Patents and Trademarks